(12) United States Patent  (10) Patent No.: US 6,666,554 B2
Mulvey  (45) Date of Patent: Dec. 23, 2003

(54) PROTECTIVE EYEWEAR KIT

(76) Inventor: Deborah C. Mulvey, 4521 Newport Ave., San Diego, CA (US) 92107

(*) Notice: Subject to any disclaimer, the term of this patent is extended or adjusted under 35 U.S.C. 154(b) by 0 days.

(21) Appl. No.: 10/033,018

(22) Filed: Dec. 27, 2001

(65) Prior Publication Data

US 2003/0123022 A1 Jul. 3, 2003

(51) Int. Cl.⁷ .................................................. G02C 1/04
(52) U.S. Cl. ........................ 351/107; 351/41; 351/44; 351/62; 351/138; 351/106
(58) Field of Search ....................... 351/41, 44, 83, 351/86, 88, 103–109, 111, 114, 124, 128, 136–138, 140, 148–152, 154, 62; 2/436

(56) References Cited

U.S. PATENT DOCUMENTS

| 2,384,867 | A | * | 9/1945 | Williams ..................... 351/104 |
| 3,209,366 | A | * | 9/1965 | Lindblom .................... 351/130 |
| 3,649,106 | A |   | 3/1972 | Hirschmann, Jr. |
| 3,756,704 | A | * | 9/1973 | Marks .......................... 351/60 |
| 3,944,344 | A |   | 3/1976 | Wichers |
| 4,515,448 | A |   | 5/1985 | Tackles |
| 4,704,015 | A | * | 11/1987 | Grendol et al. ............. 351/137 |
| 4,963,013 | A |   | 10/1990 | Bononi |
| 4,997,267 | A | * | 3/1991 | Morrison et al. ........... 351/128 |
| 5,187,503 | A | * | 2/1993 | Hilton ......................... 351/124 |
| 5,323,189 | A |   | 6/1994 | Contreras |
| 5,386,254 | A |   | 1/1995 | Kahaney |
| 5,523,805 | A | * | 6/1996 | Kuipers et al. ............. 351/103 |
| 5,745,210 | A |   | 4/1998 | Biernat, Jr. et al. |
| 5,969,786 | A |   | 10/1999 | Marcum |
| 6,196,676 | B1 | * | 3/2001 | Tabacchi ...................... 351/41 |
| 6,282,727 | B1 | * | 9/2001 | Lindahl ......................... 2/428 |
| 6,386,705 | B1 | * | 5/2002 | Chen .......................... 351/136 |

FOREIGN PATENT DOCUMENTS

WO   WO 91/17468   * 11/1991   ................. 351/103

* cited by examiner

Primary Examiner—Huy Mai
(74) Attorney, Agent, or Firm—Donn K. Harms

(57) ABSTRACT

An assembled or user assembleable and configurable eyewear kit to assemble protective eyewear adapted to the facial structure of the user and the environment in which the device will be used. The device features a frame member and two temple members for support over the ears of the user. The lenses chosen by the user are cooperatively engaged with the frame member and slideable thereon to the correct position in front of the eyes. An attachable nose bridge provides nose support for the frame member and attaches to the sides of the lenses. Optional side shields and seals between the users face and the assembled eyewear device may also be attached.

16 Claims, 2 Drawing Sheets

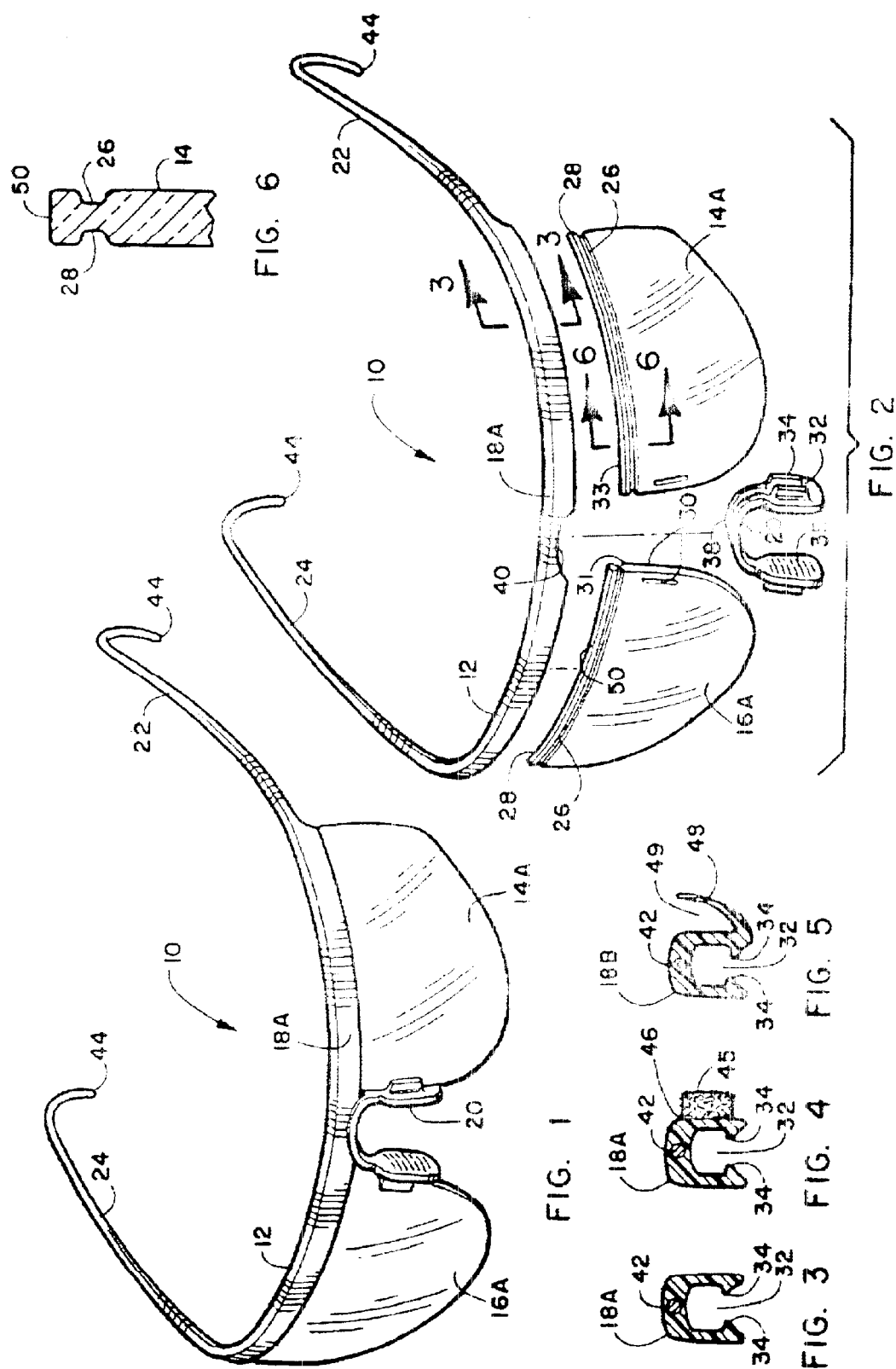

PROTECTIVE EYEWEAR KIT

FIELD OF THE INVENTION

This invention relates to the field of eyewear with regard to the safety and protection of the eyes of an individual in an environment where the eyes may become vulnerable to unforeseen damage, as in excessive light rays, random particles, random fluids, or damaging gasses. This invention also relates to an economical, versatile, and disposable kit that can easily be adapted to different sizes and levels of eye protection.

BACKGROUND OF THE INVENTION

This invention describes a new and unique comfortable Protective Eyewear Kit that is versatile, and may be adapted to different individual sizes and levels of eye protection. The inventor, with her experience of working in an operating room, has found that the disposable eye protection provided is not comfortable and does not provide adequate sealing for the eyes of those involved in the procedures. With the increasing danger of working in areas of contaminating fluids the eyes are extremely vulnerable. More laser surgery is being performed in the operating rooms, where side shielding of the eyes is another problem of those participating in the surgery.

Additionally those providers of protective or disposable eyewear go on the presumption that one size fits all, with all people having the same size head and their eyes are the same distance apart, which is not the case. Traditionally, protective eyewear is generally the same size and does not form an adequate seal around the periphery of the lenses against the face. When different sizes are available, there must be a large quantity of all the sizes available and they do not conform to the head of the wearer, generally resting on the nose and ears of the individual, leaving the eyes exposed from all directions except from the front. Often noxious gasses and odors, though they do not cause sever damage to the eyes can make the eyes tear, interfering with the vision at critical times.

An added benefit of the Protective Eyewear Kit is that it may be used in a procedure where an individual is required to wear a cover over a single eye that will limit the light entering the eye or not let any light in at all. With this unique invention, each lens is easily replaceable and may be interchanged with an opaque or black lens if required. Translucent, opaque or black side shields can also be added to protect against stray side light during laser treatments or used to keep other intrusive light from reaching the sides of the eyes.

U.S. Pat. No. 5,386,254 of Alan Kahaney describes a multi-combination sunglass assembly having a one-piece sunglass lens, an elongated lens support frame, left and right temple members, and hinge member for detachably securing the temple members to the respective left and right ends of the lens support frame. One version has flexible temple members that have hook loop fastening material secured to their ends so that they may be wrapped entirely around the wearers' head. A second version has adjustable temple members having a bendable ear-engaging portion. The nose-pad assembly has a structure that allows the sunglasses to be adjusted vertically to suit different shaped faces. Although these sunglasses are form fitting, taking the shape of the curvature of the face, they have a single lens that in no way will effectively form a seal surrounding the eyes. They are not set up for the varying number of multi-purpose safety features disclosed herein.

U.S. Pat. No. 3,994,344 of Max F. Wichers describes a spectacle structure having a plurality of flexible portions formed in head engaging components wherein the flexible portions permit unidirectional bending of the head engaging components of the specific structure thereby conforming to and exerting inward direct pressure on the head of the person to support the spectacle structure thereon with the absence of support by the nose and ears. This patent deals with the structure of the spectacle frame endeavoring to make the wearing of eyeglasses more comfortable and does not refer to the multi-purpose safety features of the disclosed by the Protective Eyewear Kit.

U.S. Pat. No. 5,745,210 of Stanley J. Biernat, Jr. et al. teaches of a an integral frame piece with front portion and two temple portions positioned on opposite ends of the front portion wherein the integral frame piece is a continuous metallic wire having super-elastic properties, and having no hinge mechanism. This patent describes the use of unique materials in combination to create a hinge-less frame for eyeglasses, but is not involved with eyeglasses that conform to the head or with any safety features.

U.S. Pat. No. 4,963,013 of Walter H. Bononi describes protective spectacles having a protective shield, fitted in the temple region, to protect the eyes from dust, etc., coming from the side. The protective shields are firmly connected by the upper edge region to the associated spectacle earpiece. It is thus pivoted away together with the earpiece. Although this patent describes a pair of safety glasses, they are the conventional flat shape across the lenses, not conforming to the head. The safety shields are not removable and the glasses are not capable of forming any form of seal around the eyes.

U.S. Pat. No. 5,323,189 of Oscar F. Contreras describes an adjustable pair of eyeglasses that retain the precise adjustment during long periods of wear. Described is an apparatus and method providing adjustment of the rim separation at the bridge of the frame of the eyeglasses and for adjusting the effective length of the temple between the shoulders and bow of the frame. It is interesting that this inventor has realized that all people do not have the same space between their eyes and that spacing has an effect on the comfort and fit of the eyeglasses. This inventor has addressed the problem mechanically by creating a mechanism that performs the task well, but he is using it on a conventional flat pair of eyeglasses, not those conforming to the shape of the head of the wearer. With this shape there is no means of sealing the area around the glasses and no way to add side shields.

U.S. Pat. No. 4,515,448 of George Tackles teaches of sunglasses having transparent planes extend in frusto-conical planes. The sunglass frame construction permits ease of plane removal and replacement. This patent deals primarily with the frusto-conical shape of a light pair of sunglasses that are shaped to the contour of the wearers' head, but not dealing with the safety features required, and do not indicate that there was any intent that they were to be used as safety glasses.

U.S. Pat. No. 3,649,106 of Jack B. Hirschmann describes a reinforced spectacle temple including a reinforced wire enclosed within front and rear sections of plastic of relatively different properties. The front section is hard and resistant to deformation, while the rear section is soft and readily formable manually with the wire to fit the ear and head of the wearer. This patent deals with one segment of a standard pair of eyeglasses and does not deal with any form of a complete pair of safety eyeglasses.

U.S. Pat. No. 5,969,786 of Steven R. Marcum tells of lightweight portable eye protectors with strategically located pads to prevent the edges of the lens of the eye protector from pinching the wearers' face, while still allowing the eye protector assembly to be easily collapsed to fit within a small portable container. This is truly a unique form of eye protection, but it goes on the premise that one size fits all with no means of adjustment, and no way to adapt them for different degrees of eye protection.

Consequently there exist a need for a kit form of eye protection that can be tailored to the needs of the individual for different levels of eye protection and also be adjustable to fit a wide range of head sizes along with varying spaces between the eyes. Additionally this Protective Eyewear Kit has been designed so it can be disposable when used in extreme environments.

SUMMARY OF THE INVENTION

The disclosed device creates a functional kit form of eye protection that can be readily adjustable, comfortable, conforming to the shape of the wearers' head and fulfilling the need for adequate eye protection, even in extreme environments. Although directed herein toward the medical field it must be understood that through the development of this invention it has become readily apparent that this Protective Eyewear Kit has many uses in other fields where varying degrees of eye protection is required, along with being useful as a unique style of adjustable sunglasses, and it must not be assumed that this patent is directed only to the medical field.

The preferred embodiment of the eye protection kit is comprised of a flexible molded plastic frame member with a malleable wire formed within the molded plastic frame member that will conform to the shape of the wearers' head. A channel with opposing barbs translates across the lower edge of the frontal section over the eyes to the temple areas on both sides allowing the lenses to slide laterally, with a depression centrally located above the nose. The plastic coated malleable wire continues from the temple area to the distal ends past the ear location of a large individual. The plastic coated malleable wire allows that the frame can be made to conform to any shape or size of the head, even contouring in the nose bridge area and staying in the shape that it has been formed, to be cut off at the distal ends when they are too long. The plastic coated malleable wire can easily be formed into the conventional shape to wrap around the ears. The barbs in the channel above the eye and back to the temple areas on the flexible molded plastic frame member retain the lenses that have mating grooves on the front and back surface along the top edge. When inserted into the channel, the lenses can be adjusted laterally with respect to the wearers' eye location and head size. The lenses will have a radial contour and can be adjusted closer together so that the glasses will ride higher up on the brow creating a better seal when needed. A cushioned nose pad bridge unit, or optional separate nose pads, will be supplied in the kit and will have a similar channel with barbs that will attach to mating grooves in the front and back surfaces of the lens in the area adjacent to the nose when inserted into the flexible molded plastic frame member channel. The crossing bridge of the nose pad bridge unit will fit into the depression centrally located on the flexible frame member.

The Protective Eyewear Kit will contain a foam-sealing strip with an adhesive surface attachable along the surface of the flexible molded plastic frame member resting against the wearers' head from the left temple to the right temple. Additionally, the kit will contain a pair of die cut foam seals with an adhesive backing that can be attached on the back surface of the lenses along the lower edge, forming a cheek seal. This foam seal will be placed adjacent to the nose pads, translating along the lower edge back to the temple area. A complete seal is not recommended due to the fact that the eyes require ventilation, and a small orifice at the back of each lens is the position least vulnerable to entry and will supply adequate air movement.

An alternate embodiment of the sealing means across the flexible molded plastic frame member will be a sweat sealing edge turned upwardly along the back surface of the flexible frame member. This sealing edge will form a cushion against the brow while retaining any sweat and directing it to the sides away from the eyes of the wearer. Raising the glasses higher on the brow will increase the effectiveness of the sweat sealing means with the increased curvature directing moisture to the sides. A similar sweat sealing means with a sealing edge will be available to seal the lower edge of the lenses to the cheek, locking into grooves in the lenses. This form of cheek seal would have a channel with barbs similar to the flexible molded plastic frame member and would engage within grooves along the lower edge of the lenses.

The Protective Eyewear Kit will also contain a set of side shields that can either be opaque, translucent or black. These shields will have grooves on both sides on the upper edge similar to the lenses and will fit into the flexible molded plastic frame member being retained by the barbs in the channel conforming to the edge of the lens. The kit will have optional opaque or black lenses available to be used after optical surgery. The kit will also have a set of elastic straps with loops sewn in the ends and a hook-loop attachment means at the other distal ends. When the protective eyewear needs to be pulled tightly against the face, the malleable plastic coated wire ends can be inserted through the loops in the straps and the end portion of the frames bent to retain the straps with the hook-loop attachment at the back of the head. These Protective Eyewear Kits will be available with any number of various combinations of the protective devices as required by different circumstances.

An object of this invention is to create protective eyewear that will give maximum protection in severe environments, Another object of this invention is to create a protective eyewear that can be adjusted to fit comfortably on individuals with a wide range of head sizes.

Another object of this invention is to create protective eyewear that will conform closely to the contours of a persons' face.

A further object of this invention is to create protective eyewear that will adjust the lenses laterally to the spacing between persons' eyes.

An additional object of the invention is to create a unique style of protective eyewear that can be used as adjustable sunglasses.

Yet another object of this invention is to create protective eyewear that can be fitted with a sealing means around the periphery of the separate lenses to conform to the different shapes of faces, while still being able to adjust laterally for optimum sealing and ventilation of the eyes.

Still another object of the invention is to create protective eyewear that can be fitted with side shields with different degrees of opacity.

An additional object of this invention is to create protective eyewear that can have either lens replaced with a special lens at different degrees of opacity.

Still another object of this invention is to create a Protective Eyewear Kit holding several different articles that will adapt the device for different levels of protection.

A further object of this invention is to create a Protective Eyewear Kit that will be disposable when used in extreme environments.

The invention accordingly comprises the features of construction, combination of elements, and arrangement of parts that will be exemplified in the construction hereinafter set forth, and the scope of the invention will be indicated in the claims.

BRIEF DESCRIPTION OF THE DRAWING FIGURES

The accompanying drawings, which are incorporated in and form a part of this specification, illustrate embodiments of the invention and together with the description, serve to explain the principles of the invention.

FIG. 1 is a perspective view of an assembled pair of one embodiment of the Protective Eyewear Kit.

FIG. 2 is an exploded perspective view of one embodiment of the Protective Eyewear Kit.

FIG. 3 is a cross section through the channel of the flexible molded plastic frame member.

FIG. 4 is a cross section through the channel of the flexible molded plastic frame member and the foam-sealing strip with an adhesive back.

FIG. 5 is a cross section through the channel of the flexible molded plastic frame member with the sweat seal.

FIG. 6 is a cross section through the top edge of one of the lenses showing the locking grooves.

DETAILED DESCRIPTION OF THE PREFERRED EMBODIMENTS

Figure 8:
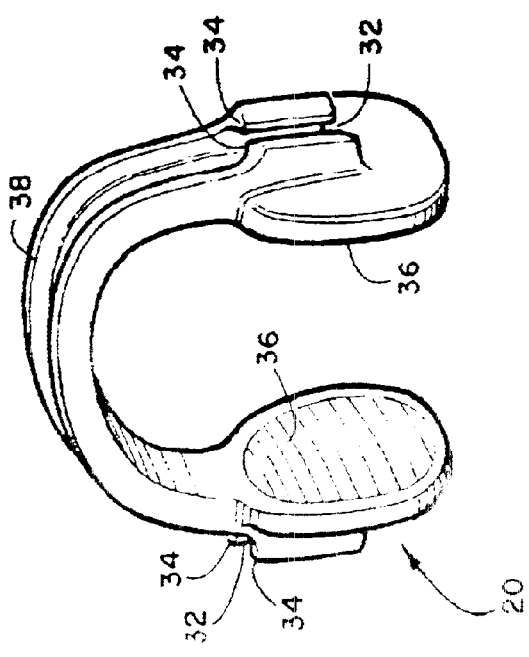
FIG. 8 is a perspective view of the nose pad bridge unit.

Referring now to the drawing FIG. 1 showing a perspective view of an assembled preferred embodiment of the Protective Eyewear Kit 10 which is user assembleable and configurable from supplied parts and composed of flexible molded plastic frame member 12, a left lens 14A and a right lens 16A beneath the channel section 18A. The nose pad bridge unit 20 is shown in place. The left temple 22 and right temple 24 consisting of plastic coated malleable wire are shown in the conventional hook around the ear shape.

FIG. 2 is an exploded perspective view of one embodiment of the Protective Eyewear Kit 10, with the lenses 14A and 16A extended to reveal the front top edge groove 26 and the back top edge groove 28 that lock into the channel section 18A allowing a means of attachment of the lenses to the frame member 12 and also a means to allow the lenses to slide laterally to an infinite number of positions between the endpoint where the left temple 22 and right temple 24 attach to the frame member 12 and the center point on the frame member 12 where the nose pad bridge unit 20 would attach, for adjustment to the facial dimensions of the user. Nose pad grooves 30 are located on the front and back surfaces of lenses 14A and 16A adjacent to the nose pad bridge unit 20. Nose pad bridge unit 20 has a small channel 32 with opposing barbs 34 to lock into grooves 30 on the back of each of the nose pads 36. A bridge 38 spans between the two nose pads 36 to fit into the depression 40 in the channel section 18A. As noted above the device could be supplied in a kit form where the user or wearer assembles the device from various lenses 14a and 16a, frame members 12, and left temple 22 and right temple 24 and nose pad bridge units 20. Or, the device could be supplied assembled but being modular in configuration it would allow the user to replace parts that wear out or are damaged, or to re configure the device to fit their facial structure by sliding the lenses in their slideable engagement or by adding and subtracting new parts that might be supplied in the kit in larger or smaller dimensions to accommodate larger or smaller facial dimensions. The result being user configurable eyewear in whether supplied assembled or in parts of a kit.

FIGS. 3, 4, and 5 are different embodiments of the channel section 18A and 18B shown in cross section views. FIG. 3 is a cross-section view of the basic channel section 18A with the channel 32 and the two opposing barbs 34 that lock into grooves 26 and 28 so that lenses 14A and 16A will slide laterally. Malleable wire 42 translates continuously from the distal end 44 of the temple 22, through the channel section 18A to the distal end 44 of temple 24.

Figure 7:
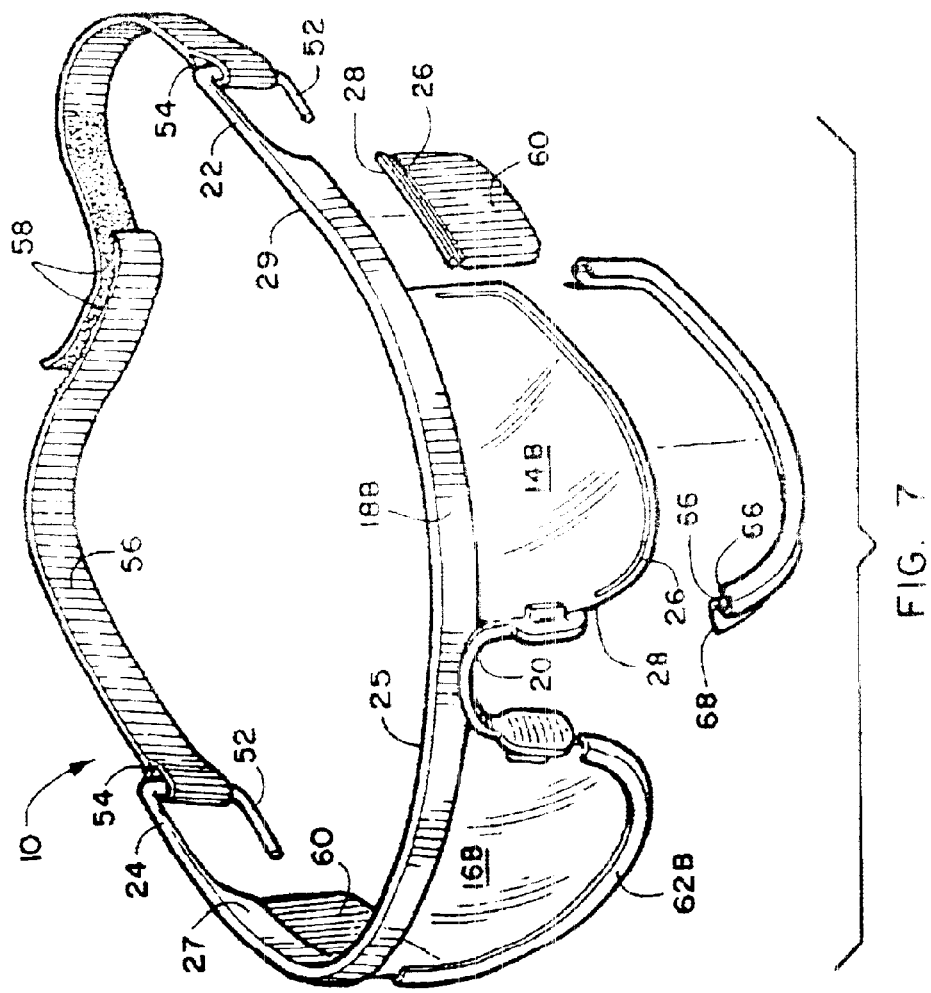
FIG. 7 is a partially exploded perspective view of an alternate embodiment of the Protective Eyewear Kit with the lower sweat seal and one side shield removed and the plastic coated malleable wire temple section bent to restrain the set of elastic straps.

FIG. 4 depicts the same channel cross-section 18A with the incorporation of the foam seal 45 and adhesive back 46 providing a means of attachment of the seal 45. The seal 45 would be provided in different configurations so that said seal could be attached using means of seal attachment such as the adhesive 46 to one or a combination of surfaces from a group of surfaces of said user configurable eyewear apparatus including, the interior surface of said frame member 25, said inner surface of the first temple member 27 and said inner surface of said second temple member 29, the interior surface of said first lens 31 and said interior surface of said second lens 33 about the perimeter edge composed of the two sides and bottom edge of both lenses. Or these various parts could be supplied with the seal 45 attached, or not, and assembled for the situation for use. FIG. 5 depicts an alternate embodiment of the channel cross-section 18B with a sweat seal 48 to seal and channel moisture to the sides of the face keeping it from entering the eyes. FIG. 6 is a cross-section view of a single lens 14A on the top edge 50 illustrating the location of the grooves 26 and 28 that are locked into channel 32 by opposing barbs 34. FIG. 7 is a partially exploded perspective view of an alternate embodiment with the left temple 22 and the right temple 24 cut short and bent into a "U" shaped configuration 52 to accommodate the loops 54 of the elastic straps 56. Adjusting the elastic straps 56 with the hook-loop attachment means 58 creates tension pulling the protective eyewear against the face to enhance the sealing ability. FIG. 7 also illustrates the extension of the channel section 18B to accommodate side shields 60 locking into channel 32, being able to slide laterally for adjustment. Side shields 60 will be available in opaque, translucent or black. Alternate embodiment of the lenses 14B and 16B will have grooves 26 and 28 for a means of attachment of a cheek seal 62A that incorporates a channel 64, opposing barbs 66 and sweat seal 68. Sweat seal 62B will be a mirror image of sweat seal 62A for the right lens 16B.

Figure 9:
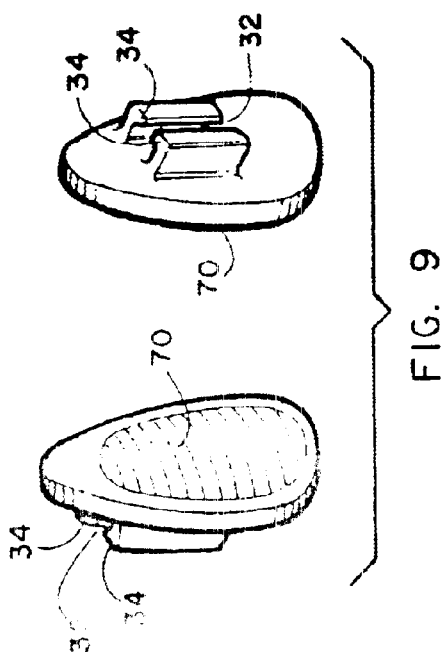
FIG. 9 is a perspective view of a pair of separate nose pads.

FIG. 8 is a perspective view of the nose bridge unit 20 with FIG. 9 illustrating a perspective view of two separate nose pads 70 that have a channel 32 with opposing barbs 34 to lock into grooves 30 on lenses 14A and 16A or lenses 14*b* or 16B.

While the present invention has been described herein with reference to particular embodiments thereof, a latitude of modification, various changes and substitutions are intended in the foregoing disclosure, and it will be appreciated that in some instance some features of the invention will be employed without a corresponding use of other features without departing from the scope of the invention as set forth.

What is claimed is:

1. A user configurable eyewear apparatus kit assembleable by the user, comprising:

a frame member having first and second ends, a center point, a top edge surface a bottom edge surface and an inner surface;

a first temple member having an interior surface, an outer surface, an upper edge and a lower edge, said first temple member attached at a first end to said first end of said frame member at a first corner point and terminating in a distal end;

a second temple member having an inner surface, an outer surface, an upper edge, and a lower edge, said second temple member attached at a first end to said second end of said frame member at a second corner point and terminating in a distal end;

a first lens, said first lens having a top edge, a bottom edge, two side edges, an interior surface area and an exterior surface area;

a second lens, said second lens having a top edge, a bottom edge, two side edges, an interior surface area and an exterior surface area;

means to attach said top edge of said first lens and said top edge of said second lens in a slidable engagement with said bottom edge surface of said frame member comprising:

a slot formed in said bottom edge of said frame member, said slot having opposing barbs extending into said slot;

a first groove formed into said interior surface area of said first lens and said second lens adjacent to said top edge;

a second groove formed into said exterior surface area of said first lens and said second lens adjacent to said top edge; and, said barbs dimensioned to cooperatively engage both said first groove and said second groove;

said first lens slidable to an infinite number of positions between said first corner point and said center point;

said second lens slidable to an infinite number of positions between said second corner point and said center point; and whereby said first lens and said second lens may be attached to said frame member and independently adjusted to the wearer's facial structure by sliding said first lens and said second lens to different positions.

2. The user configurable eyewear apparatus kit of claim 1 additionally comprising:

a nose pad bridge unit;

said nose pad bridge unit being generally U shaped and having a top edge and two side edges; and means of attachment of said top edge of said nose pad bridge unit to said frame member substantially at said center point whereby said user may assemble eyewear dimensioned to fit the user's facial structure from a plurality of kit parts.

3. The user configurable eyewear apparatus kit of claim 2 additionally comprising:

means of cooperative engagement of one each of said two side edges of said nose pad bridge unit to one of said side edges of said first lens and one of said side edges of said second lens respectively.

4. The user configurable eyewear apparatus of claim 3 additionally comprising:

a seal positioned between the wearer's face and said user configurable eyewear apparatus when attached to said eyewear apparatus, a seal positioned between the wearer's face and said user configurable eyewear apparatus when attached to said eyewear apparatus; and means of attachment of said seal to one or a combination of surfaces from a group of surfaces of said user configurable eyewear apparatus including, said interior surface of said frame member, said inner surface of said first temple member and said inner surface of said second temple member, said interior surface of said first lens and said interior surface of said second lens.

5. The user configurable eyewear apparatus kit of claim 3 additionally comprising:

a U shaped indent in said bottom edge surface of said frame member, said U shaped indent dimensioned to cooperatively engage with said top surface of said edge of said nose pad bridge.

6. The user configurable eyewear apparatus kit of claim 3 additionally comprising:

side shields attachable to one or both of said first temple member and said second temple member.

7. The user configurable eyewear apparatus kit of claim 2 wherein said means of attachment of said top edge of said nose pad bridge unit to said frame member substantially at said center point comprises a slot in said top edge of said nose pad bridge unit frictionally engaging said frame member substantially at said center point.

8. The user configurable eyewear apparatus of claim 2 additionally comprising:

a seal positioned between the wearer's face and said user configurable eyewear apparatus when attached to said eyewear apparatus, said seal attachable using means of seal attachment, to one or a combination of surfaces from a group of surfaces of said user configurable eyewear apparatus including, said interior surface of said frame member, said inner surface of said first temple member and said inner surface of said second temple member, said interior surface of said first lens and said interior surface of said second lens.

9. The user configurable eyewear apparatus kit of claim 2 additionally comprising:

a U shaped indent in said bottom edge surface of said frame member, said U shaped indent dimensioned to cooperatively engage with said top edge of said nose pad bridge unit.

10. The user configurable eyewear apparatus kit of claim 2 additionally comprising:

side shields attachable to one or both of said first temple member and said second temple member.

11. The user configurable eyewear apparatus kit of claim 1 additionally comprising:

a seal positioned between the wearer's face and said user configurable eyewear apparatus when attached to said eyewear apparatus; and means of attachment of said seal to one or a combination of surfaces from a group of surfaces of said user configurable eyewear apparatus including, said interior surface of said frame member, said inner surface of said first temple member and said inner surface of said second temple member, said interior surface of said first lens and said interior surface of said second lens.

12. The user configurable eyewear apparatus kit of claim 1 additionally comprising:

side shields attachable to one or both of said first temple member and said second temple member.

13. The user configurable eyewear apparatus kit of claim 1 wherein said means to attach said top edge of said first lens and said top edge of said second lens in a slideable engagement with said frame member comprises:

a slot formed in said bottom edge of said frame member; and said slot sized to frictionally engage said first lens and said second lens at their respective top edges when inserted therein.

14. The user configurable eyewear apparatus kit of claim 1 wherein said frame member and said first temple member and said second temple member are formed as a unitary structure.

15. The user configurable eyewear apparatus kit of claim 14 wherein said frame member and said first temple member and said second temple member are formed of malleable material and bendable by the wearer to a desired shape.

16. The user configurable eyewear apparatus kit of claim 1 additionally comprising:

cheek seals;

means of attachment of said cheek seals to said side edges and said bottom edges of said first lens and said second lens.

* * * * *